US00PP36459P2

(12) United States Plant Patent
van den Hoogen

(10) Patent No.: US PP36,459 P2
(45) Date of Patent: Feb. 18, 2025

(54) ***VERONICA* PLANT NAMED 'ALLVM1725'**

(50) Latin Name: ***Veronica longifolia* X *Veronica spicata***
Varietal Denomination: ALLVM1725

(71) Applicant: Wilhelmus T. J. van den Hoogen, Cuijk (NL)

(72) Inventor: Wilhelmus T. J. van den Hoogen, Cuijk (NL)

(73) Assignee: ALLPLANTS HOLDING B.V., Cuijk (NL)

( * ) Notice: Subject to any disclaimer, the term of this patent is extended or adjusted under 35 U.S.C. 154(b) by 0 days.

(21) Appl. No.: 18/739,305

(22) Filed: Jun. 10, 2024

(51) Int. Cl.
*A01H 5/02* (2018.01)
*A01H 6/68* (2018.01)

(52) U.S. Cl.
USPC ..... Plt./251

(58) Field of Classification Search
USPC ..... Plt./251
See application file for complete search history.

(56) References Cited

U.S. PATENT DOCUMENTS

PP35,052 P2 * 3/2023 van den Hoogen ..... A01H 6/68
Plt./251

* cited by examiner

*Primary Examiner* — Susan McCormick Ewoldt
(74) *Attorney, Agent, or Firm* — C. Anne Whealy

(57) ABSTRACT

A new and distinct cultivar of *Veronica* plant named 'ALLVM1725', characterized by its upright plant habit; moderately vigorous growth habit and moderate growth rate; freely basal branching habit; relatively small dark green-colored leaves; freely flowering habit; long and dense inflorescences with numerous purplish pink-colored flowers; good performance as a garden plant; and good postproduction longevity as a cut flower.

2 Drawing Sheets

Figure 1:
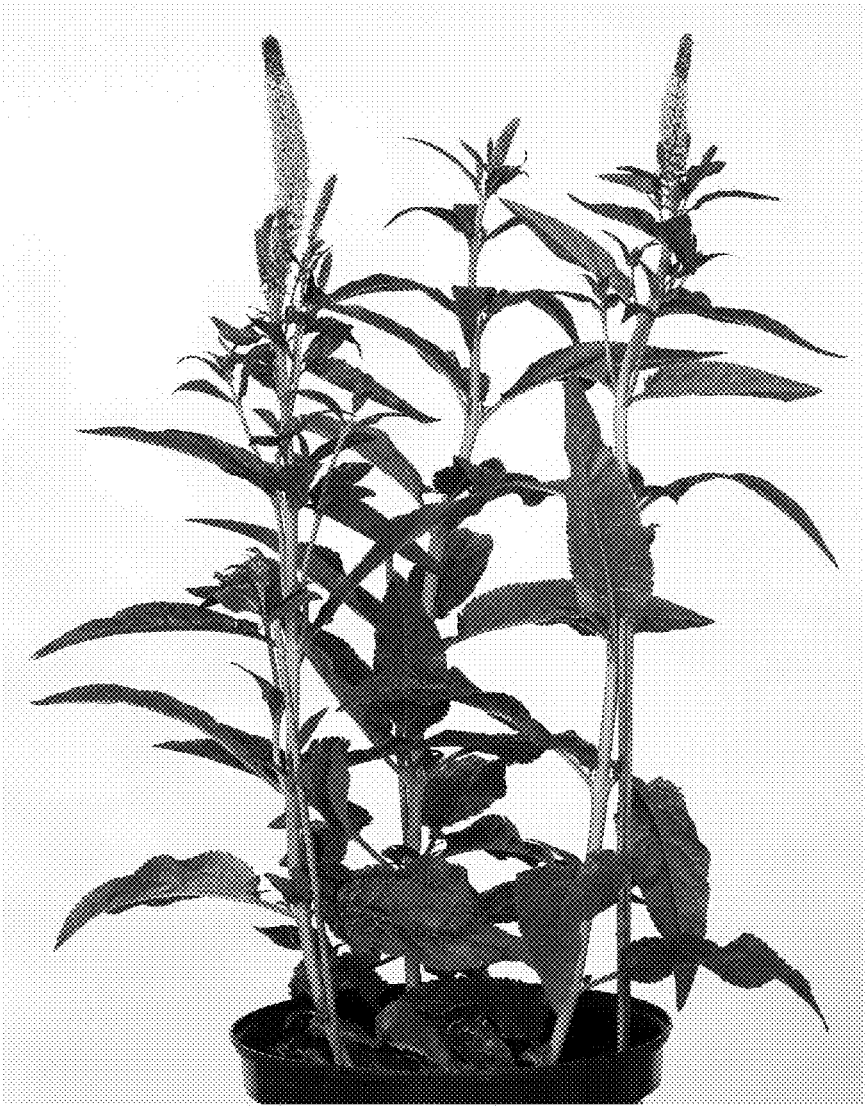

Botanical designation: *Veronica longifolia* X *Veronica spicata.*

Cultivar denomination: 'ALLVM1725'.

STATEMENT REGARDING PRIOR DISCLOSURES BY THE INVENTOR/APPLICANT & ASSIGNEE

An European Community Plant Breeder's Rights application for the instant plant was filed by the Assignee, Allplants Holding B.V. of Cuijk, The Netherlands on Mar. 22, 2023, application number 2023/0712. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Veronica* plant, botanically known as *Veronica longifolia* X *Veronica spicata*, typically grown as a garden plant and hereinafter referred to by the name 'ALLVM1725'.

The new *Veronica* plant is a product of a planned breeding program conducted by the Inventor in Cuijk, The Netherlands. The objective of the breeding program is to create new attractive *Veronica* plants with attractive flowers and good garden performance.

The new *Veronica* plant originated from an open-pollination in June 2016 of a proprietary selection of *Veronica longifolia* X *Veronica spicata* identified as code number 1-2013-75-21, not patented, as the female, or seed, parent with an unknown selection of *Veronica longifolia* X *Veronica spicata* as the male, or pollen, parent. The new *Veronica* plant was discovered and selected by the Inventor as a single flowering plant from within the progeny of the stated open-pollination in a controlled nursery environment in Cuijk, The Netherlands in August 2017.

Asexual reproduction of the new *Veronica* plant by terminal stem cuttings in a controlled environment in Cuijk, The Netherlands, since November 2017 has shown that the unique features of this new *Veronica* plant are stable and reproduced true to type in successive generations.

SUMMARY OF THE INVENTION

Plants of the new *Veronica* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'ALLVM1725'. These characteristics in combination distinguish 'ALLVM1725' as a new and distinct *Veronica* plant:

1. Upright plant habit.
2. Moderately vigorous growth habit and moderate growth rate.
3. Freely basal branching habit.
4. Relatively small dark green-colored leaves.
5. Freely flowering habit.
6. Long and dense inflorescences with numerous purplish pink-colored flowers.
7. Good performance as a garden plant and good post-production longevity as a cut flower.

Plants of the new *Veronica* differ primarily from plants of the female parent selection in flower color as flowers of plants of the new *Veronica* are darker purplish pink in color than flowers of plants of the female parent selection.

Plants of the new *Veronica* can be compared to plants of *Veronica longifolia* 'Allenjoyce', not patented. In side-by-side comparisons, plants of the new *Veronica* differ primarily from plants of 'Allenjoyce' in the following characteristics:

1. Leaves of plants of the new *Veronica* are smaller than leaves of plants of 'Allenjoyce'.
2. Plants of the new *Veronica* have longer inflorescences than plants of 'Allenjoyce'.
3. Flowers of plants of the new *Veronica* are darker purplish pink in color than flowers of plants of 'Allenjoyce'.

BRIEF DESCRIPTION OF THE PHOTOGRAPHS

The accompanying colored photographs illustrate the overall appearance of the *Veronica* plant showing the colors as true as it is reasonably possible to obtain in colored reproductions of this type. Colors in the photographs may differ slightly from the color values cited in the detailed botanical description which accurately describe the actual colors of the new *Veronica* plant.

The photograph on the first sheet (FIG. 1) comprises a side perspective view of a typical flowering plant of 'ALLVM1725' grown in a container.

Figure 2:
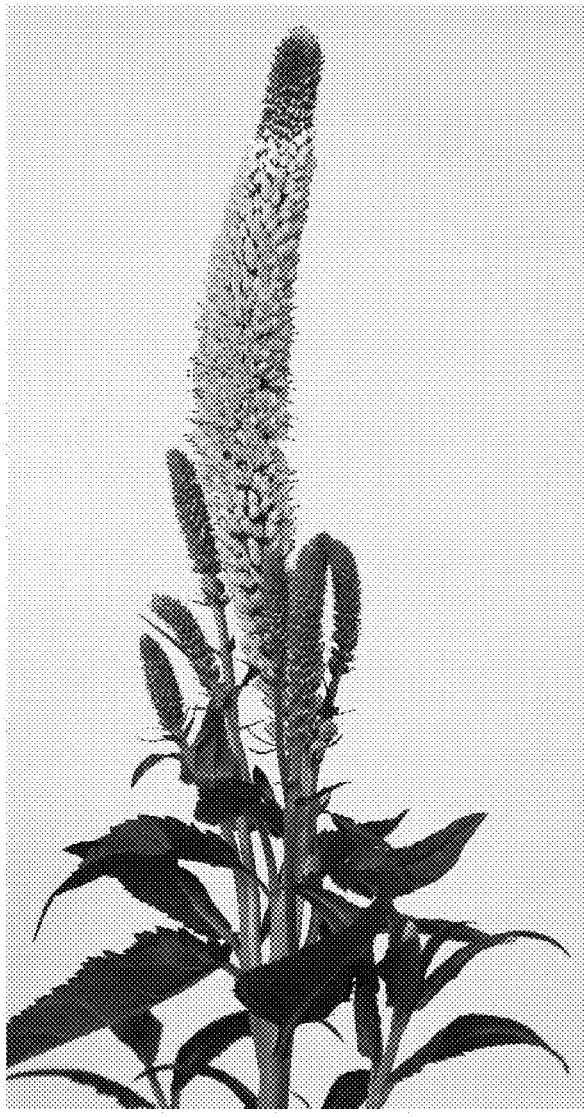

The photograph on the second sheet is a close-up view of typical inflorescences (FIG. 2) of 'ALLVM1725'.

DETAILED BOTANICAL DESCRIPTION

Plants used for the aforementioned photographs and following description were grown in ground beds and in 21-cm containers during the spring in a outdoor nursery in Cuijk, The Netherlands and under cultural practices typical of commercial *Veronica* production. During the production of the plants, day temperatures ranged from 0° C. to 25° C. and night temperatures ranged from −5° C. to 15° C. Plants were four months old when the photographs and the description were taken. In the following description, color references are made to The Royal Horticultural Society Colour Chart, 2015 Edition, except where general terms of ordinary dictionary significance are used.

Botanical classification: *Veronica longifolia* X *Veronica spicata* 'ALLVM1725'.

Parentage:

*Female, or seed, parent*.—Proprietary selection of *Veronica longifolia* X *Veronica spicata* identified as code number 1-2013-75-21, not patented.

*Male, or pollen, parent*.—Unknown selection of *Veronica longifolia* X *Veronica spicata*, not patented.

Propagation:

*Type cutting*.—Terminal stem cuttings.

*Time to initiate roots, summer*.—About two weeks at temperatures ranging from 10° C. to 25° C.

*Time to produce a rooted young plant, summer*.—About 28 to 34days at temperatures ranging from 10° C. to 25° C.

*Root description*.—Fine, fleshy; typically white in color, actual color of the roots is dependent on substrate composition, water quality, fertilizer type and formulation, substrate temperature and physiological age of roots.

*Rooting habit*.—Freely branching; dense.

Plant description:

*Plant type*.—Herbaceous perennial suitable as a garden plant and as a cut flower.

*Plant and growth habit*.—Upright plant habit with long and dense inflorescences; overall plant shape, broadly oblong; moderately vigorous growth habit and moderate growth rate.

*Plant height, soil level to top of foliar plane*.—About 47.2 cm.

*Plant height, soil level to top of floral plane*.—About 54.5 cm.

*Plant width*.—About 38.8 cm.

*Lateral branch description*.—Branching habit: Freely branching habit with about three basal stems, each with about two secondary branches; pinching enhances lateral branching potential. Length (excluding inflorescence): About 42.9 cm. Diameter: About 7 mm. Internode length: About 5.8 cm. Strength: Strong. Aspect: Erect to about 5° from vertical. Texture and luster: Smooth, glabrous; slightly glossy. Color, developing: Close to 144A. Color, developed: Close to 144B to 144C.

Leaf description:

*Arrangement*.—Opposite or in whorls of three, simple.

*Length*.—About 14.8 cm.

*Width*.—About 5.1 cm.

*Shape*.—Lanceolate to narrowly ovate; flat to slightly reflexed; slightly carinate.

*Apex*.—Acute.

*Base*.—Truncate.

*Margin*.—Serrate; not lobed.

*Texture and luster, upper surface*.—Smooth, glabrous; slightly rugose; slightly glossy.

*Texture and luster, lower surface*.—Smooth, glabrous; slightly rugose; slightly to moderately glossy.

*Venation pattern*.—Pinnate.

*Color*.—Developing leaves, upper surface: Close to 137A. Developing leaves, lower surface: Close to 146B. Fully expanded leaves, upper surface: Close to a blend of NN137A and 147A; venation, close to 146D. Fully expanded leaves, lower surface: Close to a blend of 146A and 147B; venation, close to 144B.

*Petioles*.—Length: About 2.7 cm. Diameter: About 3.5 mm by 4 mm. Strength: Strong. Texture and luster, upper surface: Smooth, glabrous; slightly glossy. Texture and luster, lower surface: Smooth, glabrous; slightly to moderately glossy. Color, upper surface: Close to 145C; margins, close to 144A. Color, lower surface: Close to 144B; margins, close to 143A.

Flower description:

*Flower arrangement and shape*.—Single campanulate flowers arranged on long and dense terminal racemes; flowers face mostly outwardly.

*Flowering habit*.—Freely flowering habit with about 540 flowers developing per inflorescence and about 4,300 flowers developing per plant during the flowering season.

*Fragrance*.—None detected.

*Natural flowering season*.—Long flowering period; plants flower continuously from the summer until the autumn in The Netherlands.

*Flower longevity*.—Individual flowers last about seven days; inflorescences last about three weeks on the plant and about two weeks as a cut flower; flowers not persistent.

*Flower buds*.—Length: About 4.5 mm. Diameter: About 2 mm. Shape: Oblong. Texture and luster: Smooth, glabrous; matte. Color: Close to N74D; developing calyx, close to 137C and proximally, 143C.

*Inflorescence height* (*length*).—About 15.6 cm.

*Inflorescence diameter*.—About 2.2 cm.

*Flower diameter*.—About 4 mm by 5 mm.

*Flower height*.—About 7 mm.

*Throat diameter*.—About 2.5 mm.

*Tube length*.—About 2 mm.

*Tube diameter*.—About 2 mm.

*Petals*.—Quantity and arrangement: Four in a single whorl; upper petal broader than the lateral and lower petal; petals fused about 50% of the petal length from the base. Length, all petals: About 4 mm. Width, upper petal: About 5 mm. Width, lateral and lower petals: About 2.5 mm. Shape, upper petal: Obovate and folded; slightly concave. Shape, lateral and lower petals: Narrowly obovate; slightly concave. Apex, all petals: Obtuse. Margin, all petals: Entire; moderately undulate. Texture and luster, all petals, upper and lower surfaces: Smooth, glabrous; matte. Texture and luster, throat: Smooth, glabrous; matte. Texture and luster, tube: Densely pubescent; matte. Color, all petals: When opening, upper and lower surfaces: Close to N74D. Fully opened, upper and lower surfaces: Close to a blend of N74C and N74D; venation, close to a blend of N74C and N74D; color does not change with subsequent development. Throat: Close to N74D; venation, close to N74D. Tube: Close to N155B; venation, close to N155B.

*Petaloids*.—Quantity and arrangement: In about 25% of flowers, a single petaloid is observed interior to the petals. Length: About 3 mm. Width: About 2 mm. Shape: Narrowly obovate. Apex: Narrowly obtuse. Base: Cuneate. Margin: Entire; moderately undulate. Texture and luster, upper and lower surfaces: Smooth, glabrous; matte. Color: When opening, upper and lower surfaces: Close to N74D. Fully opened, upper and lower surfaces: Close to a blend of N74C and N74D; venation, close to a blend of N74C and N74D; color does not change with subsequent development.

*Sepals*.—Quantity and arrangement: Four arranged in a single whorl and fused at the base. Length: About 1.25 mm to 2 mm. Width: About 1 mm. Shape: Ovate. Apex: Acute. Base: Broadly cuneate, fused. Margin: Entire. Texture and luster, upper and lower surfaces: Smooth, glabrous; matte. Color: When opening, upper surface: Close to 137B; towards the base, close to 143C. When opening, lower surface: Close to 137C; towards the base, close to 143C. Fully opened, upper and lower surfaces: Close to 137A.

*Peduncles*.—Length: Primary peduncles, about 15.1 cm; secondary peduncles, about 13.6 cm. Diameter: About 4 mm. Aspect: Primary peduncles, upright; secondary peduncles, about 30° from primary peduncle axis. Strength: Strong. Texture and luster: Smooth, glabrous; slightly glossy. Color: Close to 144B.

*Pedicels*.—Length: About 1 mm. Diameter: About 0.5 mm. Aspect: About 70° from peduncle axis. Strength: Moderately strong; flexible. Texture and luster: Smooth, glabrous; slightly glossy. Color: Close to 143B.

*Flower bracts*.—None observed.

*Reproductive organs*.—Stamens: Quantity per flower: If present, one. Filament length: About 3.5 mm. Filament color: Close to N74D. Anther size: About 1 mm by 1.5 mm. Anther shape: Broadly sagittate; dorsifixed. Anther color: Close to 182C and 182D. Pollen amount: None observed. Pistils: Quantity per flower: One. Pistil length: About 6 mm. Stigma diameter: About 2 mm. Stigma shape: Club-shaped. Stigma color: Close to 79A. Style length: About 5.75 mm. Style color: Close to 79C. Ovary color: Close to 144C.

*Seeds and fruits*.—To date, seed and fruit development has not been observed on plants of the new *Veronica*.

Pathogen & pest resistance: To date, plants of the new *Veronica* have not been noted to be resistant to pathogens and pests common to *Veronica* plants.

Garden performance: Plants of the new *Veronica* have exhibited good garden performance and to be tolerant to rain, wind, temperatures ranging from about −29° C. to about 35° C. and to be suitable for USDA Hardiness Zones 4 through 9.

It is claimed:

1. A new and distinct *Veronica* plant named 'ALLVM1725' as herein illustrated and described.

* * * * *